(12) United States Patent
Fujioka et al.

(10) Patent No.: US 6,432,094 B1
(45) Date of Patent: Aug. 13, 2002

(54) ABSORBENT ARTICLE HAVING CUSHION LAYER

(75) Inventors: Yoshihisa Fujioka; Ichiro Wada; Noriyuki Kurita, all of Kagawa (JP)

(73) Assignee: Uni-Charm Corporation, Kawanoe (JP)

(*) Notice: Subject to any disclaimer, the term of this patent is extended or adjusted under 35 U.S.C. 154(b) by 0 days.

(21) Appl. No.: 09/306,163

(22) Filed: May 6, 1999

(30) Foreign Application Priority Data

May 18, 1998 (JP) .......................... 10-135289

(51) Int. Cl.⁷ .......................... A61F 13/15; A61F 13/20
(52) U.S. Cl. .......................... 604/385.01; 604/385.101; 604/379; 604/380
(58) Field of Search .......................... 604/358, 365, 604/367, 372, 378, 380, 385.01, 385.101, 385.23

(56) References Cited

U.S. PATENT DOCUMENTS

| | | | | |
|---|---|---|---|---|
| 1,863,333 A | * | 6/1932 | Heitmeyer | 604/380 |
| 4,578,070 A | * | 3/1986 | Holtman | 604/378 |
| 5,527,300 A | * | 6/1996 | Sauer | 604/378 |
| 5,947,945 A | * | 9/1999 | Cree et al. | 604/368 |
| 5,964,743 A | * | 10/1999 | Abuto et al. | 604/385.1 |

FOREIGN PATENT DOCUMENTS

| | | | |
|---|---|---|---|
| EP | 0 366 079 A | 5/1990 | |
| EP | 0 685 212 A | 12/1995 | |
| GB | 2 042 343 A | 9/1980 | |
| GB | 2 284 831 | 6/1995 | |
| JP | S54-163137 | 12/1979 | |
| JP | S58-19252 | 2/1983 | |
| JP | H04-129553 | 4/1992 | |
| JP | H05-245961 | 9/1993 | |
| JP | H06-70957 | 3/1994 | |
| JP | H07-155596 | 6/1995 | |
| SE | WO 98/24389 | * 6/1998 | ........... A61F/13/15 |
| WO | WO 98/29074 | 7/1998 | |

OTHER PUBLICATIONS

European Search Report and Annex for EP 99 30 3832.

European Search Report and Annex for EP 00 30 2498 (01–24–01).

* cited by examiner

Primary Examiner—John G. Weiss
Assistant Examiner—Michele Kidwell
(74) Attorney, Agent, or Firm—Milbank, Tweed, Hadley & McCloy LLP (57) ABSTRACT

An absorbent article comprising a liquid-permeable top sheet, a back sheet, and an absorbent core interposed between the top sheet and the back sheet, wherein the top sheet rises upwardly from the absorbent core to have a plurality of protrusions, which extend parallel with one another in a longitudinal direction of the absorbent article, and a hydrophilic material is provided within the protrusions so as to form a cushion layer.

13 Claims, 5 Drawing Sheets

ABSORBENT ARTICLE HAVING CUSHION LAYER

FIELD OF THE INVENTION

The present invention relates to an absorbent article such as a disposable diaper, a urine absorbent pad, a sanitary napkin, or the like, particularly to an absorbent article having a surface structure material which is excellent in fitting property to a human body and which can effectively prevent side leakage.

BACKGROUND OF THE INVENTION

A conventional absorbent article such as a disposable diaper, a urine absorbent pad, a sanitary napkin, or the like generally comprises a liquid-permeable top sheet, which faces the wearer and receives excrement in use, a liquid-impermeable back sheet and an absorbent core, which is interposed between the top sheet and the back sheet and absorbs the excrement permeated through the top sheet. The absorbent core is formed by pulp and SAP (super absorbent polymer) or the like.

Among these absorbent articles, there may be a relatively bulky cushion layer constituted by hydrophilic fibers is provided between the absorbent core and the top sheet, so as to improve fitting property to the urogenital organs or environs of the wearer when it comes into contact with the crotch region of the wearer and to prevent side leakage of excrement such as urine or menses blood.

However, because the shape of the crotch region differs from one individual to another, the absorbent article having the above-mentioned cushion layer does not necessarily provide a close fit in the crotch region.

Particularly in aged people, there are remarkable differences in the shapes of the crotch region (including the urogenital organs and the inguinal region) or the abdominal region or the region between the buttocks of individuals due to shrinking of the flesh, loosening or wrinkling of the skin accompanied by age. Thus, there are many cases that a disposable diaper, a urine absorbent pad, or the like for caring for aged people cannot provide a close fit in the crotch region, etc. Further, the amount of urination of an aged person per episode is much greater than that of a baby. Thus, if the disposable diaper or the urine absorbent pad does not provide a close fit in the crotch region, urine leaks from the sides thereof, which results in wet clothes or sheets.

SUMMARY OF THE INVENTION

The present invention is to solve the conventional problems as mentioned above, and an object of the present invention is to provide an absorbent article which is easily deformed and provide a close fit in the crotch region of the wearer to conform with the shape thereof and can prevent side leakage of excrement.

The present invention is to provide an absorbent article comprising a liquid-permeable top sheet, a back sheet, and an absorbent core interposed between the top sheet and the back sheet, wherein the top sheet rises upwardly from the absorbent core to have a plurality of protrusions, which extend parallel with one another in a longitudinal direction of the absorbent article, and a hydrophilic material is provided within the protrusions so as to form a cushion layer.

The absorbent article can be used as a disposable diaper, a sanitary napkin, a urine absorbent pad, or the like, and provide a close fit in the crotch region of the wearer by the cushion layer, thereby preventing side leakage of excrement.

In order to ensure retainment of the hydrophilic material in the protrusions, it is preferred that a liquid-permeable intermediate sheet is provided between the top sheet and the absorbent core, and the top sheet and the intermediate sheet are joined at valley portions between the protrusions.

In the above construction, when joining of the top sheet and the intermediate sheet at the valley portions is carried out at intervals along the longitudinal direction, the liquid-permeable property at the valley portions is increased.

Further, when the density of the cushion layer is 0.4 g/cm$^3$ or less and the hydrophilic material is formed by hydrophilic fibers or hydrophobic fibers subjected to hydrophilic treatment, having a fineness of 1 denier or more, it becomes bulky, liquid-permeable and easily recovered or restored elastically when pressurized.

Furthermore, when the height dimension of the protrusions is 5 mm or more, the cushion layer is easily deformed depending on the shape of the crotch region of the wearer. Still furthermore, when the gap between adjacent protrusions, at the mountainsides thereof, is narrower than the width of the valley portions, excrement is easily absorbed by the protrusions.

For adapting to the shape of the crotch region, it is possible to enlarge the cross-sectional areas of the protrusions positioned near the center of the absorbent article (in a lateral direction perpendicular to the longitudinal direction) compared with the cross-sectional areas of the protrusions positioned near the sides of the absorbent article.

The back sheet is preferably liquid-impermeable.

Moreover, it is preferred that liquid barriers inferior in liquid-permeability to that of the hydrophilic material are provided inside of the protrusions along the longitudinal direction to substantially divide the hydrophilic material in two portions in the respective protrusions. Thus, excrement is easily spread to a wide range along the longitudinal direction and absorbed by the absorbent core.

This liquid barrier may be a resinous film or a hydrophobic nonwoven fabric, or else may be formed in such a manner that the intermediate sheet upwardly rises from the absorbent core, at the inside of the protrusions, or the top sheet downwardly hangs from the tops of the protrusions, at the inside of the protrusions.

BRIEF DESCRIPTION OF THE DRAWINGS

The invention will be described in more detail below by way of reference to the following drawings, in which.

DETAILED DESCRIPTION OF THE INVENTION

Figure 1:
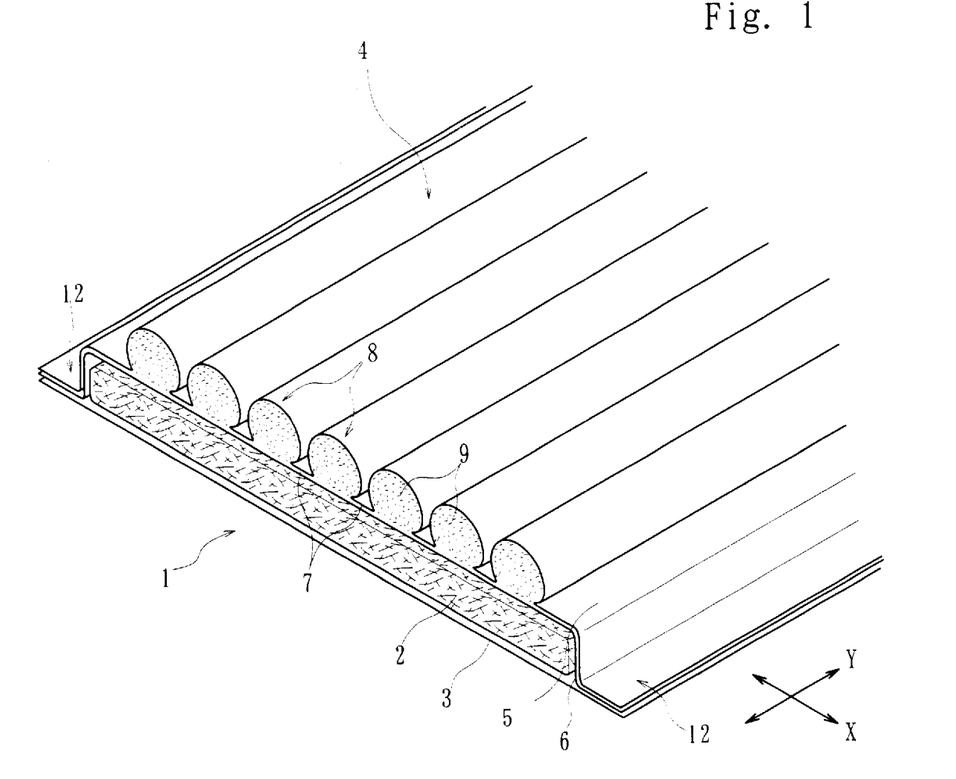
FIG. 1 is a partial perspective view including a sectional view which shows one example of an absorbent article of the present invention.
Figure 2:
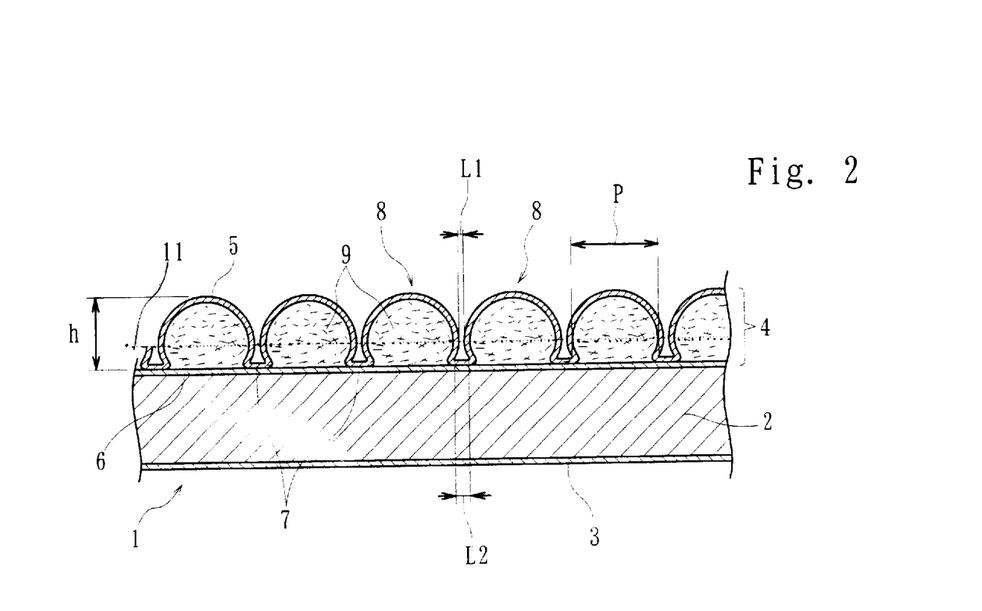
FIG. 2 is a partial sectional view of the absorbent article shown in FIG. 1.

FIG. 1 is a partial perspective view including a sectional view which shows one example of an absorbent article of the present invention, and FIG. 2 is a partial sectional view thereof. The X-axis represents the lateral direction of the absorbent article and the Y-axis represents the longitudinal direction of the same.

An absorbent article 1 comprises a surface structure material 4 which faces the wearer in use, a liquid-impermeable back sheet 3, and an absorbent core 2 interposed between the surface structure material 4 and the back sheet 3. The absorbent core 2 is formed by wrapping crushed pulp or a mixture of crushed pulp and SAP in an absorbing sheet such as tissue. The SAP can be made of polyacrylic acid, sodium polyacrylate, polyacrylamide, polyacrylonitrile, polyvinyl alcohol, an additional polymer of maleic anhydride, a polyether, a condensed polymer, a polysaccharide such as starch or cellulose, a protein such as collagen, or the like. Examples of the SAPs include: a cross-linked compound of sodium polyacrylate, a graft copolymer of starch having sodium polyacrylate or a graft copolymer of cellulose having polyacrylonitrile chains. The back sheet 3 is formed of, for example, a polyolefin resinous sheet. Incidentally, when the absorbent article 1 is used as a disposable diaper or a sanitary napkin, it is preferred that the back sheet is breathable. Moreover, when it is used as a urine absorbent pad to be used inside of a diaper, the back sheet 3 may be liquid-permeable.

The surface structure material 4 has a liquid-permeable top sheet 5 and a similarly liquid-permeable intermediate sheet 6 provided between the top sheet 5 and the absorbent core 2. The top sheet 5 and the intermediate sheet 6 comprise, for example, point bond nonwoven fabric, through-air nonwoven fabric, spun bond nonwoven fabric, or spun lace nonwoven fabric formed by hydrophobic fibers (e.g., single fibers such as of polyethylene, polypropylene or polyester and composite fibers such as of polyester and polyethylene) subjected to hydrophilic treatment, or by hydrophilic fibers (e.g., rayon fibers). The "hydrophobic fibers subjected to hydrophilic treatment" herein mentioned means a hydrophobic fiber which, for example, is made hydrophilic by treating with a surfactant; is made hydrophilic by chemically binding a chemical substance such as a monomer or a polymer having a hydrophilic group thereto; is subjected to plasma processing; is kneaded with a chemical substance having a hydrophilic group; or is made hydrophilic by treating its surface it to have a profiled section. Alternative, the top sheet 5 and the intermediate sheet 6 may comprise a resinous film such as polyethylene (PE) having a number of pores.

The top sheet 5 is joined to the intermediate sheet 6 at valley portions (or channels) 7. The valley portions 7 extend in the longitudinal direction (Y-axis direction) and are arranged at regular intervals P in the lateral direction (X-axis direction). The top sheet 5 rises upwardly from the intermediate sheet 6, between the adjacent valley portions 7, so as to form protrusions (or puckers) 8. These protrusions 8 extend along the longitudinal direction and are parallel to each other. In the individual protrusions 8, a hydrophilic material is retained between the top sheet 5 and the intermediate sheet 6 so as to form a cushion layer 9.

The hydrophilic material forming the cushion layer 9 can be formed by, for example, hydrophobic fibers (e.g., single fibers such as of polyethylene, polypropylene or polyester and composite fibers such as of polyester and polyethylene) subjected to hydrophilic treatment, or by hydrophilic fibers (e.g., rayon fibers), similar to top sheet 5 and the intermediate sheet 6. These fibers can be used as the hydrophilic material, for example, in the form of a tow, a web, or a bulky, low-density nonwoven fabric such as a through-air nonwoven fabric.

Incidentally, the hydrophilic material may be a tow of strip-shaped materials (fibers) prepared from a sheet or film, which is hydrophilic or subjected to a hydrophilic treatment.

In order to make the cushion layer 9 bulky, easily liquid-permeable and easily recovered or restored elastically when pressurized, the density of the cushion layer 9 is preferably 0.4 g/cm$^3$ or less. Further, when the hydrophilic material is formed by fibers, it is preferred that the fibers have a fineness of 1 denier or more.

Joining of the top sheet 5 and the intermediate sheet 6 at the above-mentioned valley portions 7 can be carried out by using a hot melt type adhesive, etc. Also, when the top sheet 5 and the intermediate sheet 6 contain thermoplastic fibers, joining of the top sheet 5 and the intermediate sheet 6 at the valley portions 7 can be carried out by fusion-bonding.

At the respective valley portions 7, the top sheet 5 and the intermediate sheet 6 may be joined continuously along the longitudinal direction (Y-axis direction), but preferably they are joined intermittently. That is, it is preferred that a plurality of joined portions (adhesive portions or fusion-bonding portions) are arranged at intervals along the longitudinal direction (Y-axis direction), at the respective valley portions 7, so that unjoined portions are provided between the adjacent joined portions. By employing such a construction, in the valley portions 7, excrement easily permeates through the intermediate sheet 6 to the absorbent core 2 at the unjoined portions.

Also, the height "h" of the protrusions 8 from the surface of the intermediate sheet 6 is preferably 5 mm or more to 50 mm or less, and more preferably 10 mm or more to 30 mm or less. When the height "h" of the protrusions 8 is set within the above-mentioned range, the surface structure material 4 easily fits to the uneven shape of the body of the wearer.

Also, it is preferred that a gap L1 between the adjacent protrusions 8, at mountainside portions 11 thereof, is narrower than the width L2 of the valley portion 7 (i.e., a gap between the adjacent protrusions 8, at the valley portion 7). When L1<L2, because the valley portions 7 having a relatively low liquid-permeability due to the joined portions are covered by the adjacent protrusions 8, almost all of the excrement introduced into the absorbent article 1 permeates through the protrusions 8 having a relatively high liquid-permeability. Thus, excrement can be easily absorbed by the absorbent core 2. Accordingly, more preferably L1=0, that is, it is preferred that the adjacent protrusions 8 come into contact with each other, at the mountainside portions 11.

As shown in FIG. 1, the top sheet 5 and the intermediate sheet 6 constituting the surface structure material 4, and the back sheet 3 are joined to each other at the outer region of the absorbent core 2 to form joining portions 12. At these joining portions 12, the above-mentioned respective sheets 3, 5 and 6 are joined to each other by a hot melt type adhesive or by fusion-bonding, etc.

In the absorbent article 1 according to the present invention, because the surface structure material 4 has the protrusions 8 extending parallel to each other and the bulky and low-density hydrophilic material is provided in the protrusions 8, the respective protrusions 8 deform depending on the shape of the wearer's crotch region, etc, when the surface structure material 4 is against the a wearer.

Accordingly, the surface structure material 4 provides a close fit the wearer, and as a result, excrement hardly leaks outside the absorbent article 1.

In the absorbent article 1, further, most of excrement permeates the top sheet 5, the cushion layer 9 and the intermediate sheet 6 and is absorbed by the absorbent core 2. Because this absorbent article 1 has a larger surface area for receiving the excrement, as compared with a conventional absorbent article, a higher degree of liquid-absorbing ability can be obtained. Also, in the case where a large amount of excrement is introduced into the surface structure material 4, part of the excrement, which cannot permeat into the protrusions 8 immediately, flows along the longitudinal direction (Y-axis direction) through the valley portions 7. As excrement spreads along the valley portions 7, it permeates the top sheet 5 and the intermediate sheet 6 to reach the absorbent core 2. Therefore, the excrement hardly spreads in the lateral direction (X-axis direction) and hardly leaks from the sides of the article, whereby the excrement is absorbed by the absorbent core 2 uniformly with a wide range. Accordingly, the liquid-absorbing ability of the whole absorbent article 1 can be increased and it can endure a large amount of excrement even when a thin absorbent core is used as the absorbent core 2.

Figure 3:
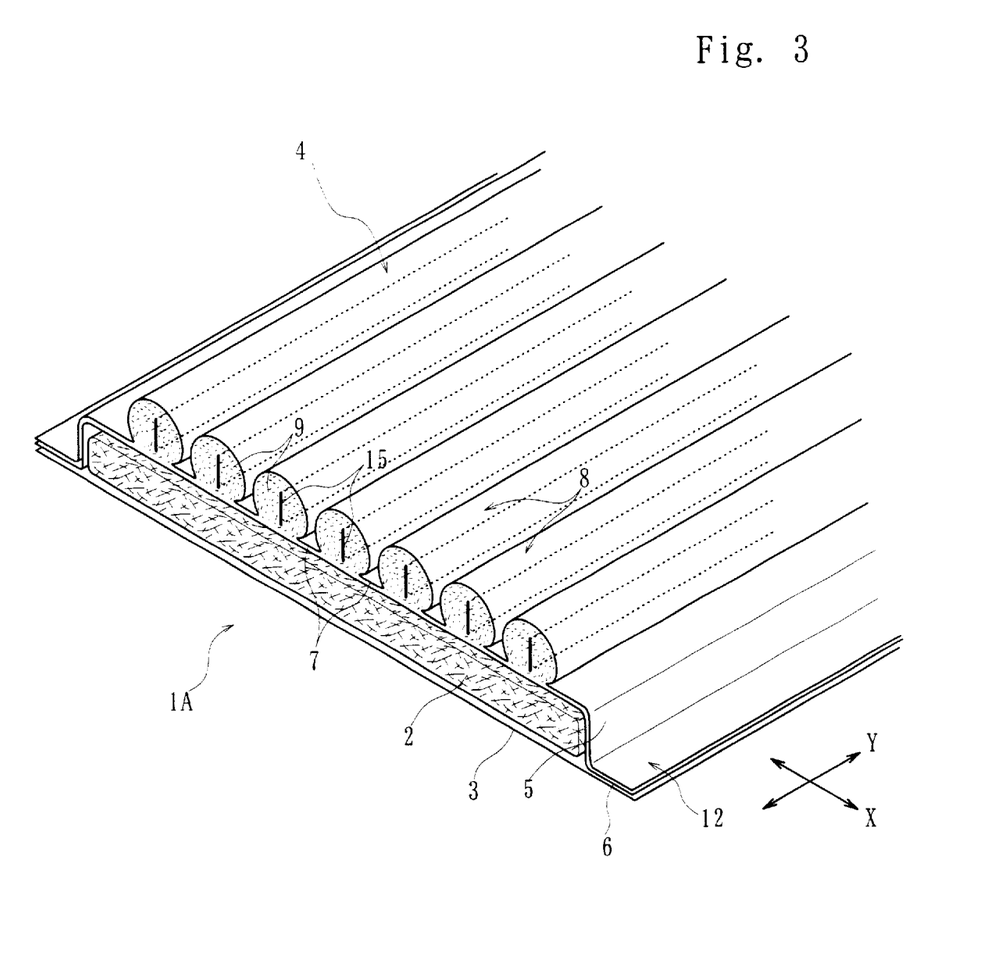
FIG. 3 is a partial perspective view showing an example in which liquid barriers are further provided to the absorbent article shown in FIG. 1.

FIG. 3 is a partial perspective view including a sectional view showing an example in which liquid barriers are further provided to the absorbent article of the present invention shown in FIG. 1.

In an absorbent article 1A, liquid barriers 15 are provided at the inside of the protrusions 8, so that the excrement permeated in the cushion layer 9 can be substantially completely dammed up in the lateral direction (X-axis direction) by the liquid barriers 15. In FIG. 3, each of the liquid barriers 15 is composed of a long strip-shaped resinous film, hydrophobic nonwoven fabric, hydrophilic nonwoven fabric, etc. Incidentally, in the case where the long strip-shaped hydrophilic nonwoven fabric is used as the liquid barrier 15, it is required that the fiber density of the hydrophilic nonwoven fabric is higher than that of the hydrophilic material constituting the cushion layer 9, so that the hydrophilic nonwoven fabric functions like a liquid barrier.

Each of the long strip-shaped liquid barriers 15 is provided all along the protrusion 8 in the longitudinal direction (Y-axis direction) so that the sheet plane thereof rises (preferably vertically) from the surface of the absorbent core 2, i.e., it substantially divides the inside of the protrusion 8 into two portions.

In the absorbent article 1A, the liquid barriers 15 prevent the excrement, which remains on the inside of the protrusions 8 because it has permeated the top sheet 5 but cannot permeate the intermediate sheet 6, from moving in the lateral direction (X-axis direction) inside of the protrusions 8. That is, excrement is inhibited to move in the X-axis direction by the liquid barriers 15 and can only flow in the Y-axis direction. Then, as it spreads along the whole absorbent article 1A by flowing in the Y-axis direction, the excrement permeates the intermediate sheet 6 and is absorbed by the absorbent core 2. Accordingly, even in the case where a large amount of excrement is introduced into the absorbent article 1A at a very small area, the excrement can be prevented from leaking from the sides of the absorbent article 1A.

Figure 4A:
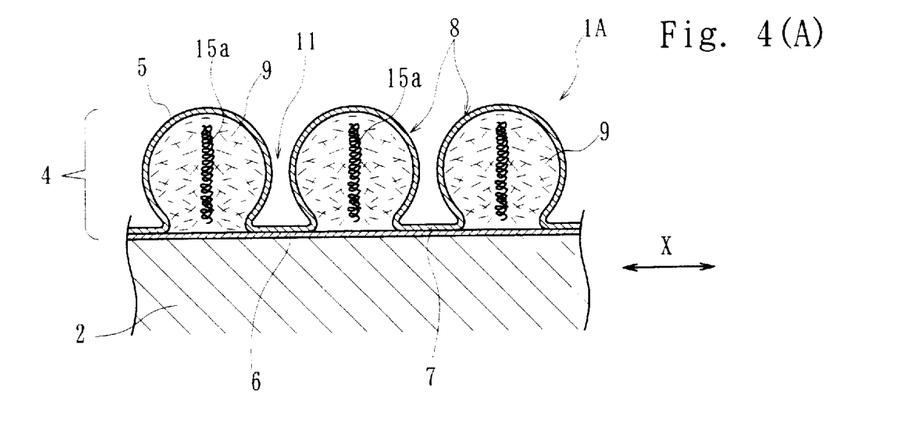
FIGS. 4(A), 4(B) and 4(C) are partial sectional views showing examples of other constructions of the liquid barriers shown in FIG. 3.
Figure 4B:
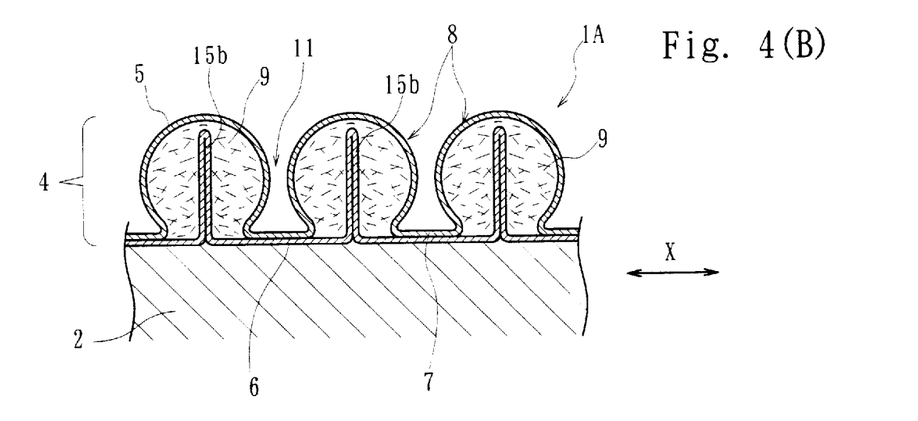
Figure 4C:
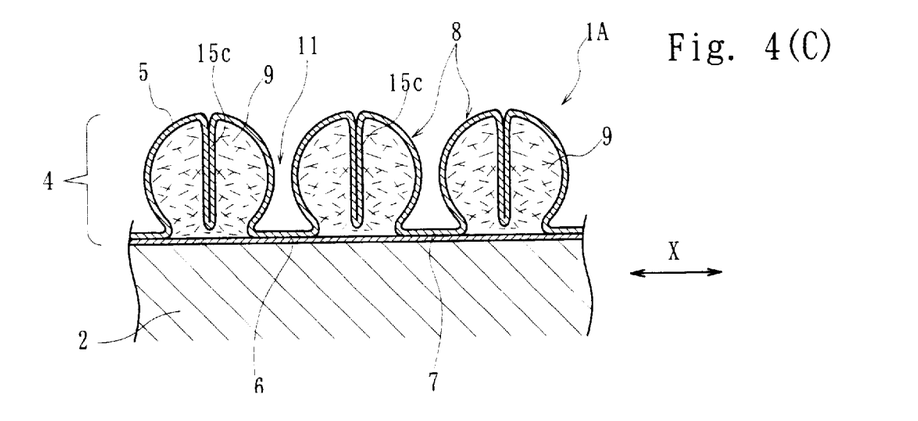

FIGS. 4(A), 4(B) and 4(C) are partial sectional views showing examples of other construction of the liquid barriers different from the example shown in FIG. 3. In FIG. 4(A), liquid barriers 15a are formed by disposing hydrophobic fibers (not subjected to hydrophilic treatment) such as composite fibers of polypropylene and polyethylene or single fibers of polypropylene or polyethylene, so as to divide the hydrophilic material in the respective protrusions 8 substantially into two portions. The fiber density of the hydrophobic fibers constituting the liquid barriers 15a is higher than that fiber density of the hydrophilic material constituting the cushion layer 9, and movement of the excrement in the lateral direction can be prevented by the liquid barriers 15a.

In FIG. 4(B), liquid barriers 15b are formed such that the intermediate sheet 6 rises upwardly from the surface of the absorbent core 2 and extends toward the tops of the protrusions 8. In FIG. 4(C), the top sheet 5 hangs down from substantially the tops of the protrusions 8 toward the absorbent core 2 whereby liquid barriers 15c are formed. Although the top sheet 5 and the intermediate sheet 6 are liquid-permeable, the top sheet 5 and the intermediate sheet 6 are folded up into two and joined together by a hot melt type adhesive, fusion-bonding or the like, at the portions of the liquid barriers 15b and 15c shown in FIGS. 4(B) and 4(C). Thus, the liquid barriers 15b and 15c are less permeable to excrement than the hydrophilic material constituting the cushion layer 9.

In the examples shown in FIGS. 4(A) to 4(C), as well as in the example shown in FIG. 3, excrement hardly spreads in the lateral direction in the protrusion 8. Instead, excrement spreads along the longitudinal direction (Y-axis direction) in the protrusion 8 whereby it is effectively absorbed by the absorbent core 2.

Figure 5A:
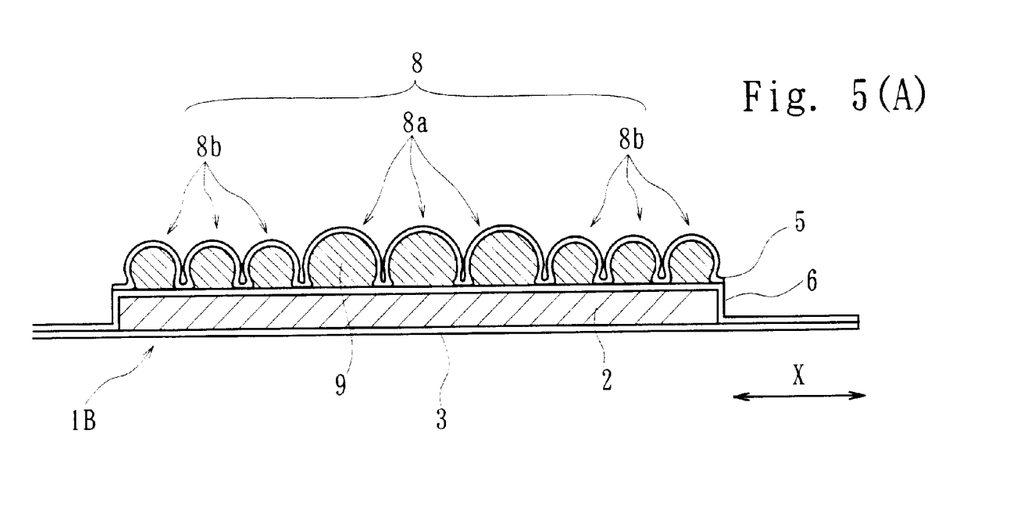
FIGS. 5(A) and 5(B) are sectional views showing examples in which cross-sectional areas of protrusions are changed in the absorbent articles shown in FIG. 1 and FIG. 3, respectively.
Figure 5B:
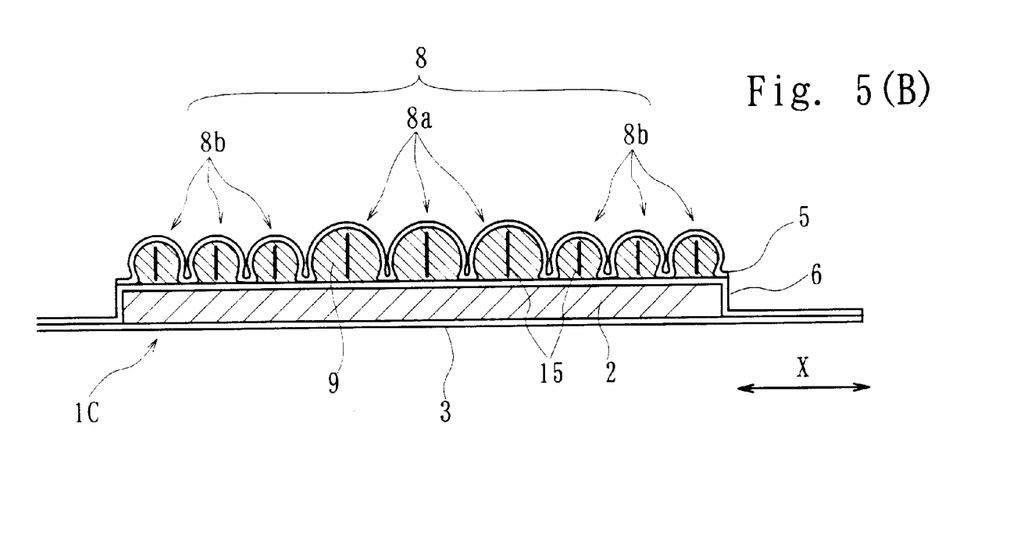

FIGS. 5(A) and 5(B) are each sectional views showing an example in which the cross-sectional areas of the protrusions 8 of the absorbent articles 1 and 1A are changed, respectively. In an absorbent article 1B shown in FIG. 5(A), the cross-sectional area of each of the protrusions 8a positioned near the center of the absorbent article in the lateral direction (X-axis direction) is greater than the cross-sectional area of each of the protrusions 8b near the sides in the lateral direction (X-axis direction).

In this case, the center protrusions 8a having a larger cross-sectional area are easily deformed depending on the shape of the crotch region or the urogenital organs. Further, because the side protrusions 8b have a smaller cross-sectional area, more protrusions can be provided near the sides in the lateral direction (X-axis direction) and having a short pitch. Thus, spread of excrement in the X-axis direction can be more effectively prevented.

Also, as in the absorbent article 1C shown in FIG. 5(B), it is of course possible to provide the liquid barriers 15 in the protrusions 5a and 8b with different cross-sectional areas.

Incidentally, if necessary, the cross-sectional area of the center protrusions may be made smaller than that of the side protrusions, contrary to the above mentioned examples. Further, the cross-sectional areas of the protrusions may be made gradually smaller or gradually larger, from the center to the sides.

Figure 6:
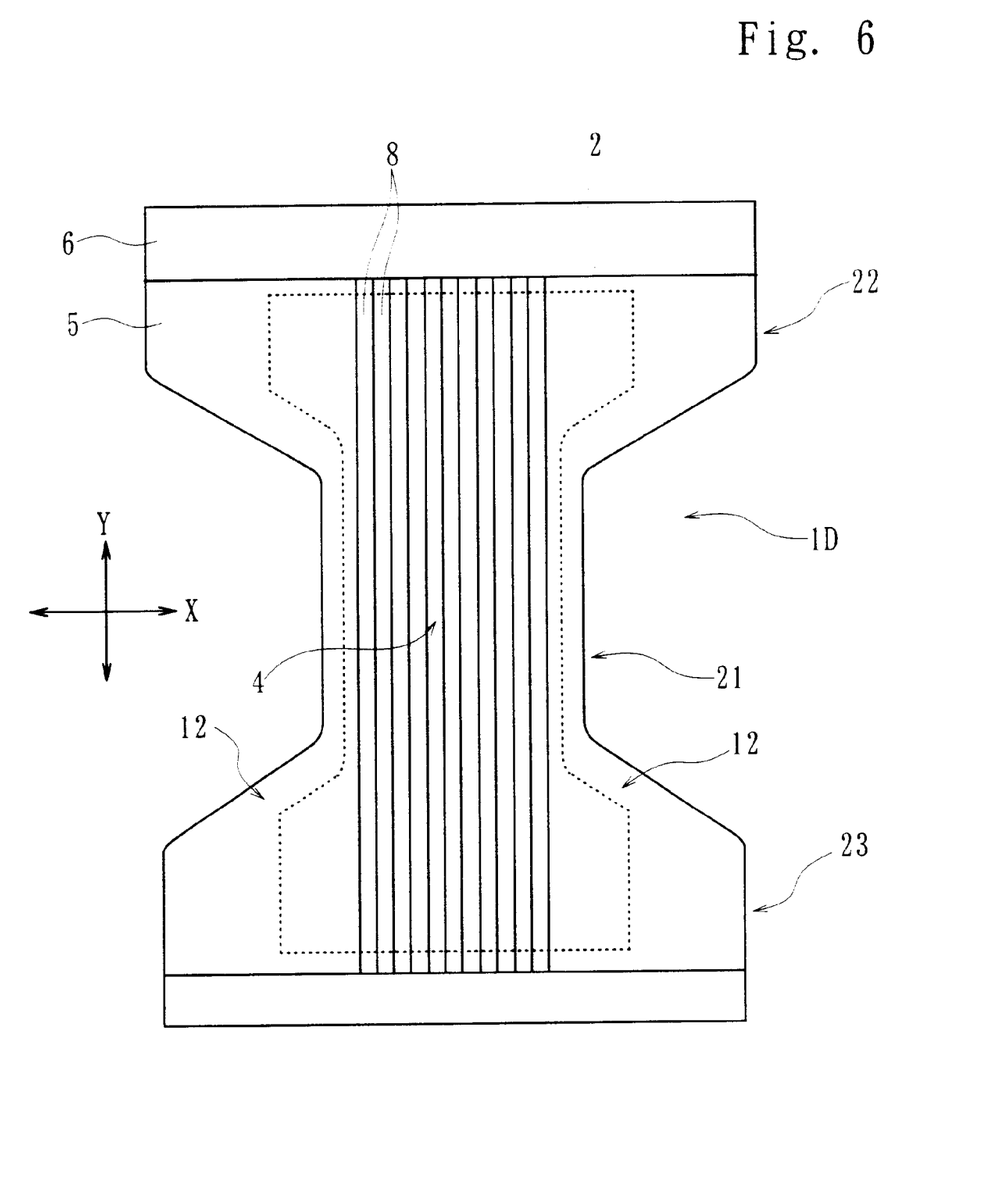
FIG. 6 is a plan view showing an example of the absorbent article of the present invention, which is formed in an hourglass shape.

FIG. 6 is a plan view showing an example of the absorbent article of the present invention with its surface structure material facing upward, in which the absorbent article is formed in an hourglass shape for use as an open-type disposable diaper. Incidentally, by changing the shape optionally, the absorbent article of the present invention may be used as a pants-shape disposable diaper, a urine absorbent pad for incontinence or a sanitary napkin.

In the absorbent article 1D, the back sheet 3, the absorbent core 2, the intermediate sheet 6 and the top sheet 5 each extend to the sides thereof, at a front portion 22 facing the abdominal side of the wearer in use and at a rear portion 23 facing the hip portion of the wearer in use, so that the absorbent article 1D has an hourglass shape. The protrusions 8 are provided so that they substantially cover the absorbent core 2 at an intermediate portion 21 facing the crotch region of the wearer in use and extend from the intermediate portion 21 to the front portion 22 and the rear portion 23. That is, the protrusions 8 continuously extend from the front portion 22 to the rear portion 23 in the longitudinal direction of the absorbent article 1D.

In the absorbent article 1D, the cushion layer is easily deformed depending on the shape of the crotch region of the wearer, and further on the shape of the abdominal portion and the buttocks of the wearer, and excrement introduced into the intermediate portion 21 easily moves to the front portion 22 and the rear portion 23, and leakage from the sides of the intermediate portion 21 can be prevented even when a large amount of excrement is introduced thereto. Incidentally, the whole shape of the absorbent article 1D shown in FIG. 6 can be variously changed depending on the uses. For example, the plane shape of the absorbent core 2 may be rectangular.

Incidentally, in the above-mentioned respective figures, the protrusions 8 linearly and continuously extend in the longitudinal direction. However, they may be formed intermittently such that the cushion layer 9 is omitted at intervals in the longitudinal direction and the top sheet 5 and the intermediate sheet 6 are joined at the omitted portions. In this case, the respective protrusions 8 should preferably have a shape which is larger in the longitudinal direction (Y-axis direction) than in the lateral direction (X-axis direction).

While in the foregoing specification the present invention has been described in relation to preferred embodiments and many details have been set forth for purpose of illustration, it will be apparent to those skilled in the art that the present invention is susceptible to additional embodiments and that certain of the details described herein can be varied considerably without departing from the basic principles of the present invention.

As used herein, "comprises" and all its grammatical forms specifies the presence of stated features, integers, steps or components, but does not preclude the presence or addition of one or more other features, integers, steps, components or groups thereof.

What is claimed is:

1. An absorbent article comprising:

a liquid permeable top sheet;

a back sheet; and an absorbent core interposed between the top sheet and the back sheet, wherein the top sheet rises upwardly from the absorbent core to have a plurality of protrusions which extend parallel with one another in a longitudinal direction of the absorbent article, and a hydrophilic material is provided within the protrusions so as to form a cushion layer, wherein the density of the cushion layer is 0.4 g/cm$^3$ or less and the hydrophilic material is formed by hydrophilic fibers or hydrophobic fibers subjected to hydrophilic treatment, having a fineness of 1 denier or more, and wherein a liquid-permeable intermediate sheet is provided between the top sheet and the absorbent core, and the top sheet and the intermediate sheet are joined at valley portions between the protrusions to hold the hydrophilic material within the protrusions.

2. The absorbent article of claim 1, wherein:

joining of the top sheet and the intermediate sheet at the valley portions is carried out at intervals along the longitudinal direction.

3. The absorbent article of claim 1, wherein:

the density of the cushion layer is 0.4 g/cm$^3$ or less and the hydrophilic material is formed by hydrophilic fibers or hydrophobic fibers subjected to hydrophilic treatment, having a fineness of 1 denier or more.

4. The absorbent article of claim 1, wherein:

a gap between the adjacent protrusions, at mountainsides thereof, is narrower than the width of the valley portions.

5. The absorbent article of claim 1, wherein:

cross-sectional areas of the protrusions positioned near centers of the protrusions in a lateral direction perpendicular to the longitudinal direction are greater than cross-sectional areas of the protrusions near sides of the protrusions in the lateral direction.

6. The absorbent article of claim 1, wherein:

the back sheet is liquid-impermeable.

7. The absorbent article of claim 1, wherein:

liquid barriers inferior in liquid-permeability to that of the hydrophilic material are provided inside of the protrusions along the longitudinal direction to substantially divide the hydrophilic material into two portions in the respective protrusions.

8. The absorbent article of claim 7, wherein:

each of the liquid barriers is a resinous film or a hydrophobic nonwoven fabric.

9. The absorbent article of claim 7, wherein:

the intermediate sheet upwardly rises from the absorbent core, inside the protrusions, to form the liquid barriers.

10. The absorbent article of claim 7, wherein:

the top sheet downwardly hangs from top protions of the protrusions, inside the protrusions, to form the liquid barriers.

11. The absorbent article of claim 1, which is a disposable diaper.

12. The absorbent article of claim 1, which is a sanitary napkin.

13. The absorbent article of claim 1, which is a urine absorbent pad.

* * * * *

UNITED STATES PATENT AND TRADEMARK OFFICE
CERTIFICATE OF CORRECTION

PATENT NO.    : 6,432,094 B1
DATED         : August 13, 2002
INVENTOR(S)   : Yoshihisa Fujioka et al.

It is certified that error appears in the above-identified patent and that said Letters Patent is hereby corrected as shown below:

<u>Title page,</u>
Item [73], Assignee, "Kawanoe" should read -- Ehime --

Signed and Sealed this

Nineteenth Day of August, 2003

JAMES E. ROGAN
*Director of the United States Patent and Trademark Office*